US008731979B2

(12) United States Patent
Dean

(10) Patent No.: US 8,731,979 B2
(45) Date of Patent: *May 20, 2014

(54) SYSTEM AND METHOD FOR SELECTING HEALTHCARE MANAGEMENT

(71) Applicant: TriZetto Corporation, Englewood, CO (US)

(72) Inventor: Val C. Dean, Franktown, CO (US)

(73) Assignee: TriZetto Corporation, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/028,710

(22) Filed: Sep. 17, 2013

(65) Prior Publication Data

US 2014/0039915 A1    Feb. 6, 2014

Related U.S. Application Data

(60) Continuation of application No. 13/170,913, filed on Jun. 28, 2011, now Pat. No. 8,548,830, which is a division of application No. 11/023,199, filed on Dec. 27, 2004, now Pat. No. 7,979,283.

(51) Int. Cl.
*G06Q 40/00* (2012.01)
*G06Q 10/00* (2012.01)
*G06Q 50/00* (2012.01)

(52) U.S. Cl.
USPC ....................................... 705/4; 705/2; 705/3

(58) Field of Classification Search
USPC .......................................................... 705/2–4
See application file for complete search history.

(56) References Cited

U.S. PATENT DOCUMENTS

| 4,567,359 | A  |   | 1/1986 | Lockwood ..................... 235/381 |
|-----------|----|---|--------|---------------------------------------|
| 5,655,085 | A  |   | 8/1997 | Ryan et al. ........................ 705/4 |
| 5,903,889 | A  |   | 5/1999 | de la Huerga et al. ................ 1/1 |
| 5,924,074 | A  |   | 7/1999 | Evans ................................ 705/3 |
| 6,208,973 | B1 | * | 3/2001 | Boyer et al. ...................... 705/2 |
| 6,456,979 | B1 |   | 9/2002 | Flagg ............................... 705/4 |
| 7,162,436 | B1 | * | 1/2007 | Eckel, Jr. .................... 705/14.67 |

(Continued)

FOREIGN PATENT DOCUMENTS

| WO | WO 94/20916 | 9/1994 | ............. G06F 19/00 |
|----|-------------|--------|-------------------------|
| WO | WO 01/69513 | 9/2001 | ............. G06F 19/00 |

OTHER PUBLICATIONS

European Search Report issued for European Patent Application 05855083.1-2201, dated Jan. 17, 2008, 11 pp.

(Continued)

*Primary Examiner* — Joseph Burgess
(74) *Attorney, Agent, or Firm* — Dawn-Marie Bey; Bey & Cotropia PLLC

(57) ABSTRACT

The present invention is directed to a system and method which allows a prospective insured to make an informed decision on healthcare insurance or a specific health care management decision by using a current medical profile to assist in their selection. Based on past medical care, as obtained from payor data, a number of different plans, each having different providers, different deductibles, different maximums, different reimbursement policies, etc., a person can make an informed decision. When a family has different payors for different family members, a proper blend of payors can be more easily selected since the payors (or a single payor) has a medical profile of each family member and also has information on providers in the network, prescription policies, deductibles, maximums, etc.

17 Claims, 2 Drawing Sheets

(56) References Cited

U.S. PATENT DOCUMENTS

| | | | |
|---|---|---|---|
| 2002/0010597 A1 | 1/2002 | Mayer et al. | 705/2 |
| 2002/0010679 A1 | 1/2002 | Felsher | 705/51 |
| 2002/0040305 A1* | 4/2002 | Nakatsuchi et al. | 705/2 |
| 2002/0049617 A1 | 4/2002 | Lencki et al. | 705/4 |
| 2002/0111835 A1 | 8/2002 | Hele et al. | 705/4 |
| 2002/0147617 A1* | 10/2002 | Schoenbaum et al. | 705/4 |
| 2002/0147867 A1 | 10/2002 | Satlow | 710/100 |
| 2003/0036683 A1 | 2/2003 | Kehr et al. | 600/300 |
| 2003/0046113 A1* | 3/2003 | Johnson et al. | 705/3 |
| 2003/0130873 A1 | 7/2003 | Nevin et al. | 705/3 |
| 2003/0191667 A1 | 10/2003 | Fitzgerald et al. | 705/2 |
| 2003/0191669 A1 | 10/2003 | Fitzgerald et al. | 705/2 |
| 2004/0039604 A1* | 2/2004 | Tallal, Jr. | 705/2 |
| 2004/0064343 A1 | 4/2004 | Korpman et al. | 705/2 |
| 2004/0117215 A1 | 6/2004 | Marchosky | 705/3 |
| 2004/0122790 A1 | 6/2004 | Walker et al. | 1/1 |
| 2004/0143462 A1 | 7/2004 | Hunt et al. | 705/3 |
| 2004/0205664 A1 | 10/2004 | Prendergast | 715/255 |
| 2005/0010446 A1 | 1/2005 | Lash et al. | 705/2 |
| 2005/0222867 A1 | 10/2005 | Underwood et al. | 705/2 |
| 2006/0100908 A1* | 5/2006 | Becker et al. | 705/3 |
| 2006/0136264 A1 | 6/2006 | Eaton et al. | 705/2 |

OTHER PUBLICATIONS

International Search Report and Written Opinion for Application No. PCT/US05/46464, dated Nov. 29, 2006.

International Search Report and Written Opinion for Application No. PCT/US05/46461, dated Oct. 23, 2006, 6 pp.

* cited by examiner

SYSTEM AND METHOD FOR SELECTING HEALTHCARE MANAGEMENT

CROSS-REFERENCE TO RELATED APPLICATIONS

The present application is a continuation of U.S. patent application Ser. No. 13/170,913, filed Jun. 28, 2011, entitled "SYSTEM AND METHOD FOR SELECTING HEALTHCARE MANAGEMENT," which is a divisional application of U.S. patent application Ser. No. 11/023,199, filed Dec. 27, 2004, entitled "SYSTEM AND METHOD FOR SELECTING HEALTHCARE MANAGEMENT," the disclosures of which are incorporated herein by reference.

TECHNICAL FIELD

This invention is related to medical systems and more particularly to systems and methods for providing assistance in making healthcare decisions, and even more particularly to a system and method for assisting in the selection of a healthcare manager.

BACKGROUND OF THE INVENTION

A problem occurs when a person is attempting to make a health care decision, such as, for example selecting a medical insurance (or even life insurance) plan suitable for that person or for that person's family. Different plans have different deductibles for different procedures. Different plans also have different healthcare providers characterized as "in-network" or "out of network" providers. Since the "proper," i.e. lowest cost, plan that meets the individual's and/or family's needs will ultimately depend upon what medical services that person (or family) will require over the life of the plan and since that information is, by definition, not known at the time of plan selection, the solution is usually a "best estimate" guess. With something as crucial to a person's physical and financial health as medical insurance, the existing system for selection of a proper plan leaves a great deal to be desired.

One example of the problem arises when a family tried to decide which medical management plan to sign up for at work. Assume both the husband and the wife each have several options. Also assume that the husband is currently seeing Doctor A for a specific illness. Also assume that the wife is of child-bearing years but they already have two children. In our example, the husband's plan is less expensive than the wife's plan and includes Doctor A. If this family were to accept the wife's plan they would pay more per month and if the husband were to continue using Doctor A he would not be reimbursed the full amount because Dr. A is not on the "in-network" list of the wife's plan. Based on the available facts, it appears that the husband's plan should be selected.

However, this analysis did not take into account the reimbursement for medications for each plan, nor did it take into account the medical costs for the two children. Also not taken into account is the likelihood of a long-term illness to a family member where medication costs, hospital reimbursements, perhaps home-care costs and certainly maximum limits could drastically affect the overall cost of medical assistance.

Also not taken into account is the fact that different types of procedures require different expertise. Thus, a particular group of medical providers may yield statistically better results than another group for treatment of a specific ailment. Thus, deciding upon a healthcare plan, or even upon a course of healthcare treatment, requires more information than is currently available to a potential healthcare purchaser.

BRIEF SUMMARY OF THE INVENTION

The present invention is directed to a system and method which allows a prospective insured to make an informed decision on healthcare insurance by using a current medical profile to assist in the selection of future medical insurance. Based on past medical care, as obtained from payor data, a number of different plans, each having different providers, different deductibles, different maximums, different reimbursement policies, etc., a person can make an informed decision. When a family has different payors for different family members, a proper blend of payors can be more easily selected since the payors (or a single payor) has a medical profile of each family member and also has information on providers in the network, prescription policies, deductibles, maximums, etc.

In one embodiment there is provided a system and method for combining actual past medical payor information, as obtained from a profile of a patient's (or a patient's family) medical history, so as to help select the proper plan going forward. In an embodiment, the system will extrapolate from actual data to form an anticipated going-forward medical projection for the family. In a further embodiment, the system and method accepts data from the family concerning their own plans for the future so as to refine the medical projections, thereby further reducing the guess factor in the selection of a medical plan.

In another embodiment, options to a medical course of action are provided to a patient based upon prior experience the patient's healthcare plan has with providers in the patient's coverage area. Using such a system and method, a particular group of medical care providers may be selected for a particular procedure based on those provider's statistical data. In addition, a particular medical facility may be determined to be a better match for the patient, given the entire medical history of the patient and the past track record of the healthcare facility. Thus, in some situations it may be beneficial for the patient to go outside the network for a particular treatment.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

The forms which are filed (usually electronically) by healthcare providers for reimbursement from payors contain clinical data pertaining to the patient. In addition, health care plans use pharmacy benefit management companies (PBMs) to evaluate and pay pharmacy claims. This process of verification generates pharmacy data which then compliment the treatment and diagnostic data obtained from doctors. In addition, when a physician orders a laboratory test, the test costs are billed for either by the ordering physician or by the providing physician, such as by a radiologist. The claim for payment also goes to the payor. In some situations the actual test results will go the payor, or can be obtained by the payor in an electronic format.

The system and method described herein takes advantage of the fact that all of this data funnels through a common point and can be used to provide a comprehensive holographic view of a patient's health. Thus, in the disclosed system and method, the health plan acts as the aggregator of information pertaining to its members and that aggregated information is used to create a meaningful representation of the medical profile of the member.

Figure 1:
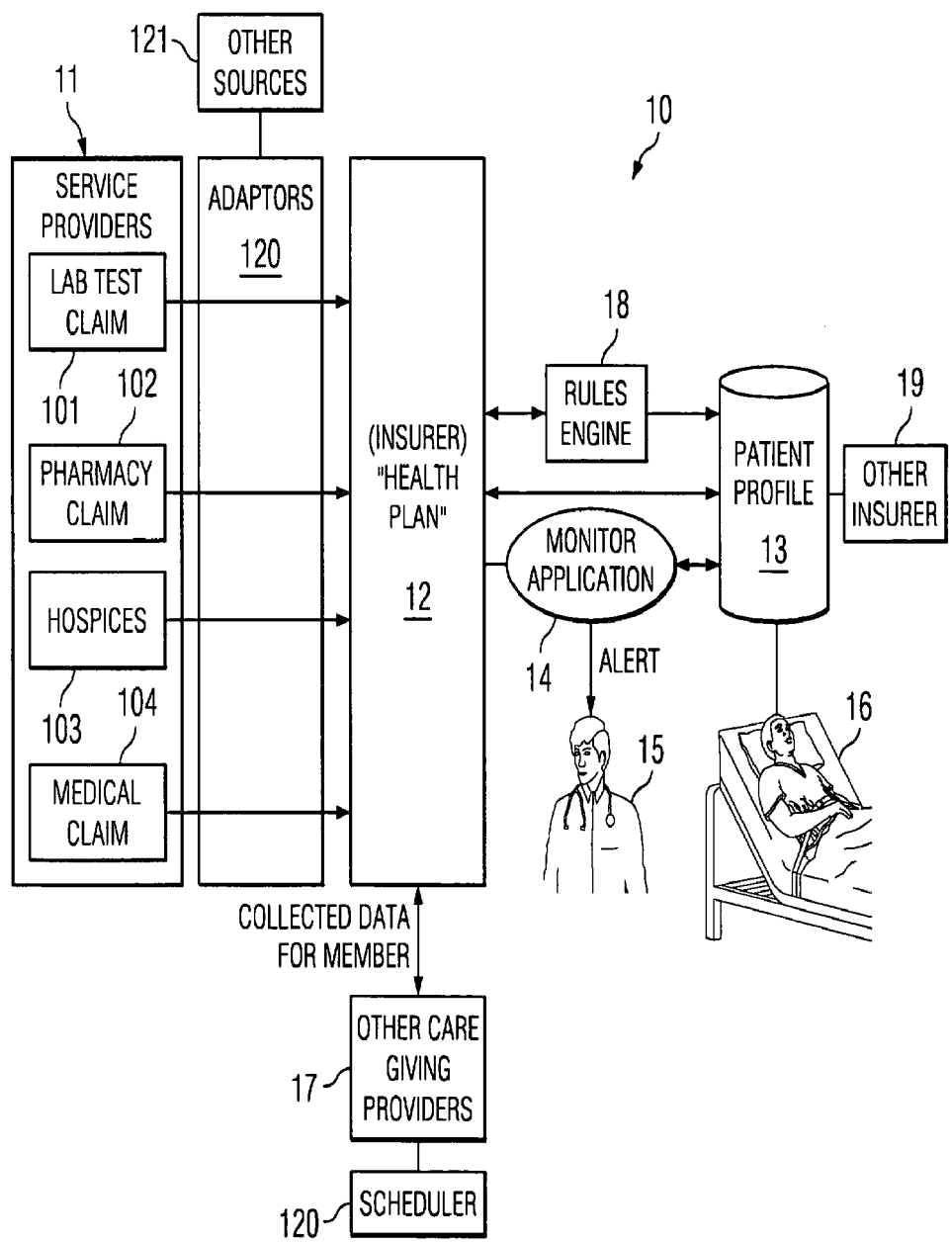
FIG. 1 is one embodiment of a system and method for consolidating medical information from a myriad of healthcare providers.

Turning now to FIG. 1, system 10 shows one embodiment of a system and method for consolidating medical information from diverse sources, such as Service Provider 11, to give a consolidated profile of a patient. Service provider 11 represents service providers which could encompass test lab 101, pharmacies 102, hospitals 103, and physicians 104. Claims from any provider are submitted to a patient's insurer 12. Others, such as the user, user's family, or even unrelated systems such as, for example, a credit card profile system, shown as 121, can also submit claims to insurer 12. At least a portion of the information coming from these various diverse sources is stored in database 13. While it is contemplated that the raw data be stored in database 13 it could be that only abstracted data (such as above or below limit data) is so stored. Also note that database 13 could accept data from other insurers 19 which could occur, for example, if a patient were to have multiple insurers (husband and wife; private and government, etc).

Assuming patient 16 used provider 15 as a primary provider but also used other providers 17 (cardiologist, diabetic specialist, obstetrician/gynecologist), it could be appropriate for any one or more of these providers to set "rules" for the patient. These rules could pertain to filling and refilling a prescription, taking and sending certain monitored readings (sugar levels, air flow, etc.), limits on certain readings, etc. These rules are stored in rules engine 18 on a patient-by-patient basis and when a rule has been attained (i.e., a certain monitored fact is outside a limit), then monitor application 14 sends a message (e-mails, telephone, fax, etc) to provider 15 (and possibly also to one or more other parties, including the patient).

Claims are submitted from various service providers, as well as the patient, and these claims may be formatted differently based on the reason for the data exchange. To handle such a situation, proper interfacing between systems is required and this is handled by adaptors, such as adapters 130.

One example of how the system and method could work is where physician A has prescribed a particular medication for a patient and physician B, possibly because that patient failed to inform physician B of the medication he/she is taking, prescribed another medication that might be dangerous when mixed with the first medication or possibly negates the effects of the first medication. In such a situation, the system would generate an alert to the patient and, if desired, to both physicians A and B. The reason the alert can be delivered is because of the composite view of a patient's medical history as obtained from payment records. Since the system is based upon data coming to a payor for reimbursement, over-the-counter medicines or medicines that are not paid for by the provider will only get into the system if the patient (or someone acting for the patient) sends in the data.

Another example would be if a patient has asthma and is asked to measure his/her peak air flow daily and to call the physician if the readings go below a certain level. Frequently patients don't follow through with the instructions or are worried about calling ("bothering") the physician. Using this system a member could go online to record his/her peak flow every day. This on-line data is then sent to the system. A rule is set up in the system that says: if air flow falls below a certain level, or if there is a significant downward trend, issue an Alert. Thus, even if the patient is not at the critical stage, alerts are sent and trouble can be averted. The physician cannot take phone calls from patients every day and calculate changes to air flow, but the provider could set the system to accept a patient's input and to call (alerts) when certain limits are met. In addition, patients can input symptoms, such as coughing, vomiting, chest pain, headaches, temperature, blood pressure, etc., and this data can be used to trigger an alert based either on a general group rule, or on parameters set individually for that patient.

Compliance by a patient is another major concern. For example, the provider asks a patient to take a medication, monitor peak air flow to lungs, check blood sugar, see a specialist, etc. In reality, the provider does not know whether the patient has complied or not. When the patient ends up in the emergency room because of failure to follow directions it is often too late for help. However, using the system and method described herein, the provider will be notified if certain values decrease or change or hit a certain level. Alerts will be generated if the values are missing, i.e., not put in for two or three consecutive days, etc. Also, missing data could be that a prescription has not been filled (or refilled on time), thereby initiating an alert.

These are all examples of the power obtained when the medical history of a patient can be generated and continually monitored based upon an abstraction of data meant for another purpose, namely payment information.

Figure 2:
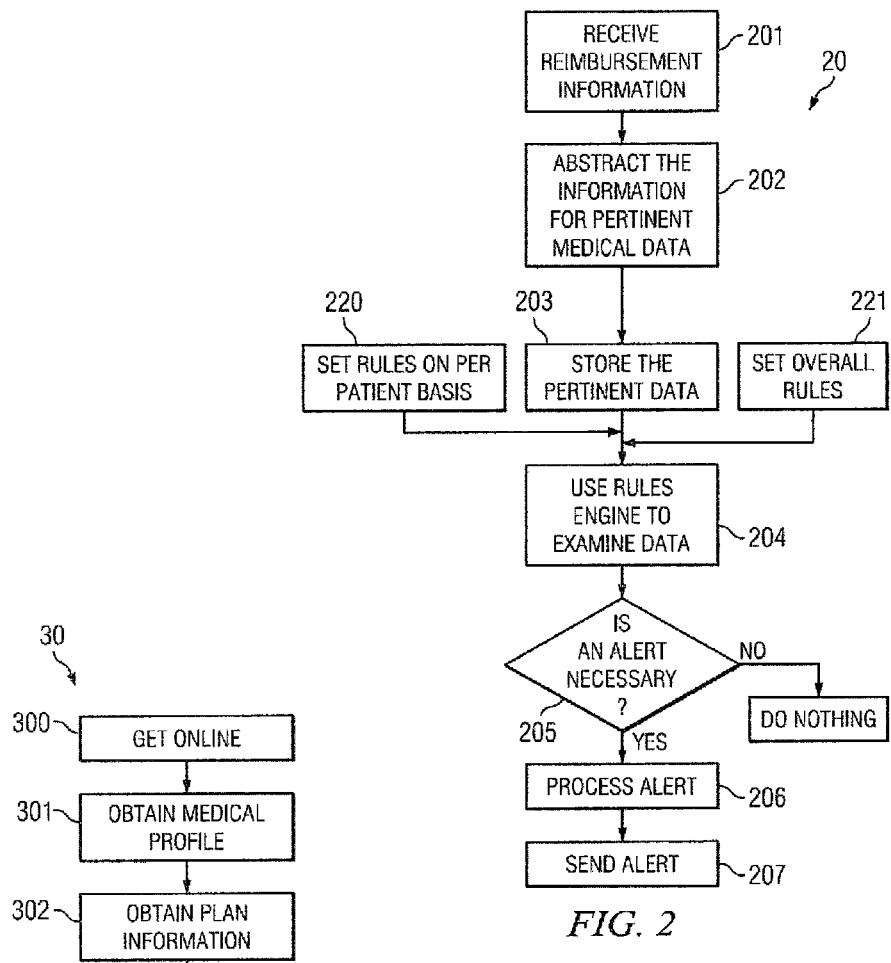
FIG. 2 is one embodiment of a method for obtaining and profiling medical information.

FIG. 2 shows one embodiment of system 20 where process 201 receives reimbursement information (a payment claim) from any one of a number of medical providers. This information contains within it enough information so that the third party payor can process the payment to determine how much will be reimbursed. This reimbursement can be sent directly to the provider or sometimes it is sent to the patient. Each such claim must contain with it enough information so that the payor can properly determine the procedure that was performed, and whether the patient is eligible for reimbursement and what the limits are. Often the provider sends minimal information that certain tests have been performed and does not send the actual test results. However, in some situations, the actual test scores are sent with the payment claim information. Pharmacies send in the prescription and sometimes also the diagnosis along with their claim information. In FIG.

1 this information is shown coming from service providers 11 and goes directly to insurer 12 but the data could pass through adapters 120 designed such that the data from each provider is converted so that pertinent data can be removed, as desired, for storage in patient profile storage 13.

In addition, process 201 will process data from a patient, such as from patient 105 (FIG. 1). This data could be test results that have been self-administered, such as blood sugar levels, peak flow levels, blood pressure, temperature, or any other measurable physiological parameter that is necessary for a medical diagnosis. In addition, a patient can input symptomatic information, such as chest pain, coughing, vomiting, or any other type of occurrence, such as blurry vision, or abdominal pain, all of which will be received by process 201 and processed to become part of the patient profile information stored in storage 13.

Process 202, either before the information is stored in patient profile 13 or thereafter, and with or without the help of adaptors 120, creates an abstract of the information to determine certain information. For example, process 202 could look at various pieces of information and conclude that a patient is a diabetic. This would be concluded, for example, by looking at the medication the patient is taking, patient hospital visits, supplied lab test results, etc., and applying rules under control of rules engine 18 (FIG. 1) to conclude that this patient is in a group of diabetics. Other types of information could lead to an abstracting of a patient so that the patient is classified as a heart patient, a pregnant patient, etc. Each of these categories could then require the further abstracting of information to determine from symptoms provided by the patient when to send an alarm.

For example, if a patient is classified as having heart failure, then upon receiving information from a patient that the patient is having night time cough, the system would, based upon process 204, determine that this patient (or his/her health care provider) needs be alerted.

The system is established such that an administrator, who could be a doctor, could establish parameters that would apply to all of the patients in the database. This information would apply to the whole population of patients falling within the rules for the group. Within each group each physician could establish specific parameters for his/her specific patients.

Process 203, as discussed, stores the pertinent data either in patient profile storage 13 or in other storage and based upon rules established by rules engine 18. Process 205 determines if an alert is necessary. If an alert should be sent, such an alert will be processed via process 206 to determine what type of an alert, who the alert should go to, and how, and will also determine what type of data should be supplied. Process 207 sends the alert to one or more providers, other third parties, or to the patient, as desired. Process 220 sets rules for the rules engine on a per-patient basis while process 221 sets rules for groups of patients. Process 204 examines the data under control of the rules engine, or any other comparison system.

Figure 3:
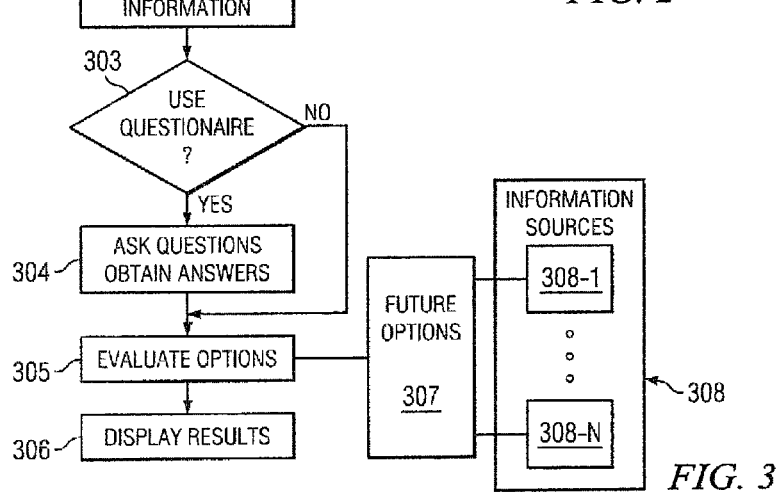
FIG. 3 is one embodiment of a method for assisting in the selection of a healthcare management plan.

Turning now to FIG. 3 there is shown method 30 whereby the person who desires to begin the process of selecting a medical reimbursement plan, or to select life insurance or other situations where the amount of money a person receives or pays is dependent upon a particular plan or policy or to determine a proper course of treatment, will get online via process 300. Process 300 can include, for example, a computer connected to the system via an Internet connection or it can be a person requesting assistance by telephone. Process 300 can, for example, run on a processor at a central location having access to patient profile data, such as patient profile 13 of FIG. 1, or the processor can run local to the patient based on downloaded (or accessed) data. The person seeking the information herein will be called the user.

Process 301 obtains medical, and medical cost profiles for the user and for any others having affinity to the user, such as the user's family or any other person that the user has responsibilities to pay the medical bills for. Process 30 also then obtains the plan information via process 302 for all of the plans that are available to the user, including those plans available to the user's spouse and perhaps even for plans that are available over-the-counter. Plan information can include, for example, medication formularies, benefits, funding mechanisms, limits, deductibles, in-network and out-of-network fees, prescription costs, co-pay charges, etc.

One option would be to use a questionnaire via process 303 to submit answers from the user via process 304 pertaining to medical factors known only to the user. For example, these questions could deal with future (or current) pregnancies or elective surgery or could even solicit symptomatic information (chest pain, etc.). The questions could also pertain to dental situations with respect to braces, and any other type of information that would bear upon the ultimate cost of health insurance. These processes could compile a patient profile consisting of medical history, preferred providers, current medications, planned medical interventions, and other pertinent information for choosing among a variety of health plan options, including the patient's financial risk profile and preferences. Process 303 can be set up for a specific anticipated procedure, such as, for example, a knee replacement procedure. In such a situation, the system would seek information about the patient's desires and concerns and, based on the patient's medical history, ask other questions pertinent to the situation at that point in time.

Once this information is gathered, i.e. the patient's profile, the plan information for several plans, answers to the questions via process 304, etc., then process 305, perhaps in conjunction with rules engine 18 of FIG. 1, or using its own processor, can evaluate the options available to the user. This evaluation is based upon the type of medication the patient is taking, the different types of diagnoses and tests that have been performed over a course of time and by reviewing the medical history of the user's family. A profile can then be established of the user and the profile can be used to help the user determine which plan would be "best" for that user, or what the various options are "likely" to cost the user over a prescribed period of time. For a particular procedure, the profile would provide options of providers and facilities for selection by the patient. In some situations it might be better for a patient to use an out-of-network doctor and select a plan that pays for a longer period of time or that handles a certain type of illness better than others, even though on the surface such a selection is counter-intuitive. In some cases, it could be beneficial for a plan to make an exception for a certain user such that the user will actually be reimbursed at the in-network reimbursement rate even though the user uses an out-of-network provider. This could also be true on a procedure-by-procedure basis. This follows since the system may determine that over the long run using out-of-network providers and/or facilities will be the most inexpensive way for the plan to operate for the given circumstances of the user's family or for a given procedure. Note that the displayed results may be by cost, by number of available providers or by other criteria.

Using the system and method discussed herein, the system can take into account the user's age, prior medical conditions, answers to questions of lifestyle and a myriad of other situations. For example, how far a user drives impacts his/her likelihood of being involved in an accident. Does the user own a boat, an airplane, what are the travel plans of the person, etc. Note that travel plans, as well as other lifestyle information are not medical information but they do have an impact on the user's medical treatment and this should be factored into the profile also. Note that this lifestyle information can come from the user or from sources external to the user, such as, for example, a reservation system or a credit card company. When all this information is evaluated by process 305, comparisons are displayed for the user via process 306. The information for such a display could be sent to the user wirelessly or by wire line, which could be wirelessly or wired to the user. Thus the information could be displayed on the screen of a computer (not shown) or communicated in an email or otherwise to the user.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method for assisting a patient with selection of at least one provider and at least one facility for an identified medical procedure comprising:
   receiving by a processor an indication of the identified medical procedure for the patient;
   accessing by the processor medical plan information for the patient, wherein the medical plan information includes in-network and out-of-network information for providers and facilities available to the patient for performing the identified medical procedure;
   evaluating by the processor the medical plan information and determining combinations of one or more providers and one or more facilities available to handle the identified medical procedure for the patient;
   providing by the processor a list of options for handling the at least one medical procedure for the patient, the options including both in-network and out-of-network options and the options being ranked according to least cost over a predetermined period of time, wherein each option includes one or more providers and one or more facilities for performing the at least one medical procedure; and
   further wherein at least one out-of-network option costs less over the predetermined period of time than one or more in-network options.

2. The method according to claim 1, wherein the options are future options that include one or more provider and one or more facility options that will be available at a future time.

3. The method according to claim 2, further comprising:
   obtaining by the processor external information from one or more sources other than the medical plan information to determine the future options.

4. The method according to claim 1, wherein the at least one out-of-network option costs less over the predetermined period of time than one or more in-network options by making an exception for reimbursement of costs for the at least one out-of-network option.

5. The method according to claim 1, wherein the medical plan information comprises information on benefits, funding mechanisms, limits, deductibles, in-network and out-of-network fees, prescription costs, and co-pay charges.

6. The method according to claim 1, wherein the medical plan information for the patient includes multiple medical plans.

7. A method for assisting a patient with selection of at least one provider and at least one facility for an identified medical procedure comprising:
   receiving by a processor an indication of the identified medical procedure for the patient;
   receiving by the processor patient-generated information in response to a medical factor questionnaire;
   accessing by the processor medical plan information for the patient, wherein the medical plan information includes in-network and out-of-network information for providers and facilities available to the patient for performing the identified medical procedure;
   accessing the patient-generated information;
   evaluating by the processor the medical plan information and the patient-generated information and determining combinations of one or more providers and one or more facilities available to handle the identified medical procedure for the patient;
   providing by the processor to the patient a list of options for handling the at least one medical procedure for the patient, the options including both in-network and out-of-network options and the options being ranked according to both least cost over a predetermined period of time and one or more applicable patient preferences determined from the evaluation of the patient-generated information, wherein each option includes one or more providers and one or more facilities for performing the at least one medical procedure; and
   further wherein at least one out-of-network option costs less over the predetermined period of time than one or more in-network options.

8. The method according to claim 7, wherein the options are future options that include one or more provider and one or more facility options that will be available at a future time.

9. The method according to claim 8, further comprising:
   obtaining by the processor external information from one or more sources other than the medical plan information to determine the future options.

10. The method according to claim 7, wherein the at least one out-of-network option costs less over the predetermined period of time than one or more in-network options by making an exception for reimbursement of costs for the at least one out-of-network option.

11. The method according to claim 7, wherein the medical plan information comprises information on benefits, funding mechanisms, limits, deductibles, in-network and out-of-network fees, prescription costs, and co-pay charges.

12. The method according to claim 7, wherein the medical plan information for the patient includes multiple medical plans.

13. A method for generating selections of at least one provider and at least one facility for an identified medical procedure comprising:
   providing to a processor an indication of the identified medical procedure for the patient and requesting generation of one or more selections for at least one provider and at least one facility for performing the identified medical procedure;

receiving a medical factor questionnaire in response the request;

providing one or more responses to a medical factor questionnaire to the processor, wherein the processor compiles patient-generated information therefrom;

receiving by the patient a list of options including combinations of one or more providers and one or more facilities available to handle the identified medical procedure for the patient, wherein the combinations are generated by the processor using medical plan information for the patient, wherein the medical plan information includes in-network and out-of-network information for providers and facilities available to the patient for performing the identified medical procedure and the patient-generated information, further wherein each option includes one or more providers and one or more facilities for performing the at least one medical procedure over a predetermined period of time, and further wherein the list includes at least one out-of-network option that costs less over the predetermined period of time than one or more in-network options.

14. The method according to claim 13, wherein the options are future options that include one or more provider and one or more facility options that will be available at a future time.

15. The method according to claim 13, wherein the at least one out-of-network option costs less over the predetermined period of time than one or more in-network options by making an exception for reimbursement of costs for the at least one out-of-network option.

16. The method according to claim 13, wherein the medical plan information comprises information on benefits, funding mechanisms, limits, deductibles, in-network and out-of-network fees, prescription costs, and co-pay charges.

17. The method according to claim 13, wherein the medical plan information for the patient includes multiple medical plans.

* * * * *